United States Patent
Watanabe et al.

(10) Patent No.: US 7,387,620 B2
(45) Date of Patent: Jun. 17, 2008

(54) WEARING ARTICLE WITH REMOVABLE PAD INSERTABLE THROUGH SUPPORTING SHEET SLIT

(75) Inventors: Maki Watanabe, Kagawa-ken (JP); Ichiro Wada, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 336 days.

(21) Appl. No.: 11/109,694

(22) Filed: Apr. 20, 2005

(65) Prior Publication Data
US 2005/0256491 A1 Nov. 17, 2005

(30) Foreign Application Priority Data
Apr. 23, 2004 (JP) .............................. 2004-127949

(51) Int. Cl.
*A61F 13/15* (2006.01)
(52) U.S. Cl. .................... 604/385.14; 604/385.19; 604/395; 604/385.11
(58) Field of Classification Search ................ 604/383, 604/385.14, 385.19, 386, 387, 395, 385.11
See application file for complete search history.

(56) References Cited

U.S. PATENT DOCUMENTS 4,834,737 A * 5/1989 Khan ..................... 604/385.14
5,069,672 A * 12/1991 Wippler et al. ......... 604/385.14
2002/0091368 A1* 7/2002 LaVon et al. .......... 604/385.14

FOREIGN PATENT DOCUMENTS

JP 1997-56746 3/1997
JP 2000-42033 2/2000

* cited by examiner

*Primary Examiner*—Jacqueline F. Stephens
(74) *Attorney, Agent, or Firm*—Lowe Hauptman Ham & Berner LLP

(57) ABSTRACT

A wearing article includes pants having a supporting sheet extending between front and rear waist regions and a body waste absorbing pad formed in its upper surface with a first opening and releasably attached to the inner side of the pants. The supporting sheet is formed with a slit through which a rear zone of the pad can be inserted. The pad is provided on its upper surface with a joined sheet having a second opening. A front zone and an intermediate zone of the pad are placed on the upper surface of the supporting sheet, the rear zone of the pad is inserted into the slit so as to be interposed between the pants and the supporting sheet, free front and rear zones are fastened to the upper surface of the supporting sheet and thereby the pad is attached to the pants by means of the supporting sheet.

11 Claims, 15 Drawing Sheets

WEARING ARTICLE WITH REMOVABLE PAD INSERTABLE THROUGH SUPPORTING SHEET SLIT

RELATED APPLICATIONS

The present application is based on, and claims priority from, Japanese Application Number 2004-127949, filed Apr. 23, 2004, the disclosure of which is hereby incorporated by reference herein in its entirety.

BACKGROUND OF THE INVENTION

The present invention relates to a wearing article comprising pants and a pad releasably attached to the pants so that the pad may absorb and retain bodily discharges.

There have already been proposed disposable wearing articles each comprising pants and an absorbent pad attached to the inner side of the pants having front and rear waist regions opposed to each other, a crotch region extending between these waist regions, a waist-hole and a pair of leg-holes, and an absorbent pad attached to the inner side of the pants so as to extend between the front and rear waist regions (see Japanese Unexamined Patent Application Publication No. 1997-56746, hereinafter referred to as "Reference 1"). The pad comprises a wearer-facing liquid-pervious topsheet, a wearer-opposing liquid-impervious backsheet and an absorbent core interposed between and bonded to these sheets. In the pad, longitudinally opposite ends of the backsheet extending beyond longitudinally opposite ends of the core are bonded to respective peripheries of the front and rear waist regions of the pants and a longitudinally middle zone of the backsheet is bonded to the crotch region of the pants. This wearing article allows bodily discharges to be absorbed through the topsheet by the core and to be retained therein.

There have already been proposed also body waste absorbent pads, each of which is longer than is wide, comprising an absorbent unit and a cover sheet wherein the absorbent unit is formed by a liquid-pervious topsheet, a liquid-impervious backsheet and an absorbent core interposed between these sheets and respective segments of the top- and backsheets extending upward from a periphery of the absorbent unit define the cover sheet so as to cover the upper surface of the absorbent unit and wherein the absorbent unit is centrally formed with an opening surrounded by the cover sheet (see Japanese Unexamined Patent Application Publication No. 2000-42033, hereinafter referred to as "Citation 2"). The cover sheet is provided around its crowning with a circularly extending stretchable elastic member contractibly attached thereto. The pad is releasably attached to the inner side of the crotch region of a diaper cover by means of pressure-sensible adhesive coated on the lower surface of the backsheet and then worn together with the diaper cover. This pad allows bodily discharges to be absorbed through the opening by the absorbent unit and retained therein. The pad contaminated with bodily discharges may be released from the diaper cover for disposal.

In the case of the wearing article disclosed by Reference 1, it is impossible to exchange the pad alone with a fresh pad after this pad has been contaminated with bodily discharges since the pad is bonded to the pants. In other words, the article as a whole should be exchanged with a fresh article. In addition, when body waste exceeds a given critical mass, this pad of prior art can not sufficiently function to absorb bodily discharges completely and an excess of bodily discharges may leak out from the pad. This is because the pad of prior art is formed therein with no space adapted to retain bodily discharges.

In the case of the pad disclosed by Reference 2, the pad is attached to the crotch region of the diaper cover so that the pad may slip down as the diaper cover slips down from its proper position. Consequently, it may be impossible for the pad to maintain itself in contact with the wearer's skin and bodily discharges may leak sideways out of the pad.

SUMMARY OF THE INVENTION

It is an object of the present invention to provide a wearing article improved so that the wearing article includes an absorbent pad adapted to absorb a large amount of bodily discharges, to be maintained in contact with the wearer's skin and to be exchanged with a fresh pad independently of a chassis.

According to the present invention, there is provided a wearing article comprising; pants having front and rear waist regions opposed to each other, a crotch region extending between these waist regions, a waist-hole and a pair of leg-holes, and a disposable body waste absorbent pad having front and rear zones and an intermediate zone extending therebetween, the pad being adapted to be releasably attached to an inner side of the pants and the front zone and the intermediate zone or at least the intermediate zone of the pad with a first opening extending through an upper surface of the pad so that body waste having passed through the first opening is contained within the pad.

The article according to the present invention further comprises the pants being provided on the inner side thereof with a supporting sheet extending between the front and rear waist regions, the supporting sheet having longitudinally opposite fixed end portions bonded to respective peripheries of the front and rear waist regions and an intermediate zone extending between the fixed end portions, and the intermediate zone of the supporting sheet being formed in a transversely middle zone thereof with an insertion slit extending in a transverse direction so that the rear zone of the pad being inserted through the insertion slit; the pad being provided on the upper surface thereof with a joined sheet attached to the upper surface of the pad and formed with a second opening contiguous to the first opening, the joined sheet having a fixed inner peripheral zone bonded to an opening's peripheral zone defining the first opening and a distal front zone extending forward from the front zone of the pad and releasably attached to the supporting sheet by means of fastener means. According to the present invention, the pad being attached to the pants by means of the supporting sheet by placing the front zone and the intermediate zone of the pad on an upper surface of the supporting sheet, inserting the rear zone of the pad through the insertion slit so as to be interposed between the pants and the supporting sheet and fastening the free front zone of the joined sheet to the upper surface of the supporting sheet by the fastener means.

The present invention may include the following preferred embodiments.

In one preferred embodiment of the present invention, said joined sheet has a distal rear zone extending over the rear zone of said pad and releasably attached to said supporting sheet by fastener means and wherein the distal front zone and the distal rear zone of said joined sheet are fastened to the upper surface of said supporting sheet by said fastener means and thereby said pad is attached to said pants by means of said supporting sheet.

In another preferred embodiment of the present invention, the pad comprises a liquid-impervious upper sheet, a liquid-impervious lower sheet and a liquid-absorbent core interposed between these sheets and the core is bonded to the lower sheet, and the joined sheet is attached to the upper surface of the upper sheet so that a space adapted to contain the body waste is formed between the upper sheet and the lower sheet.

In still another preferred embodiment of the present invention, the rear zone of the pad has a pouch-like shape which gradually broadens in the transverse direction as the pad roundly extends rearward with respect to the rear zone so that the rear zone has a body waste absorbing capacity higher than those of the front and intermediate zones of the pad.

In further another preferred embodiment of the present invention, the supporting sheet is elastically stretch-and contractable and the intermediate zone of the sheet is spaced upward from the crotch region of the pants.

In an additional preferred embodiment of the present invention, the fastener means comprise hook members attached to a lower surface of the distal front and rear zones of the joined sheet or pressure-sensitive adhesives coated on the lower surface of the distal front and rear zones of the joined sheet.

In the article according to the present invention, the front zone and the intermediate zone of the pad are secured to an upper surface of the supporting sheet as the distal front zone of the joined sheet is fastened to an upper surface of the supporting sheet and the pad is attached to the pants by means of the supporting sheet. It is ensured thereby that the movement of the pants is not transmitted directly to the pad as the prior art has been the case and therefore the pad does not follow the wearer's movement even if the pants move as the wearer moves. The pad does not slip down even if the pants slips down from the proper position around the wearer's body. Thus the pad is reliably maintained in close contact with the wearer's skin and it is unlikely that urine might be discharged outside the pad. The rear zone of the pad is interposed between the pants and the supporting sheet 35 so that the rear zone of the pad can be protected from readily collapsing and urine once absorbed by the rear zone never leaks out through the opening to the outside of the pad even when a body pressure of the wearer is exerted on the article. The article allows the pad having absorbed urine therein to be released from the pants for disposal. In this manner, the pad alone can be exchanged with a new and the pants can be reused repetitively.

In the case of the wearing article wherein the joined sheet has the distal rear zone extending over the rear zone of the pad and releasably attached to the supporting sheet by fastener means, the distal rear zone is fastened together with the distal front zone of the joined sheet to the upper surface of the distal sheet as the pad is attached to the pants. In this way, the pad can be reliably fixed to the supporting sheet.

In the case of the wearing article wherein the pad comprises the liquid-impervious upper sheet, the liquid-impervious lower sheet and the liquid-absorbent core interposed between these sheets and the core is bonded to the lower sheet, body waste received by the space can be absorbed and retained by the core so that leak of body waste out from the pad can be reliably prevented.

In the case of the wearing article wherein the rear zone of the pad has a pouch-like shape which gradually widens as the rear zone roundly extends rearward in the longitudinal direction and correspondingly the rear zone achieves an absorption capacity higher than those achieved by both the front zone and the intermediate zone of the pad, even if a relatively large amount of urine is discharged during use of the article, this amount of urine can be completely received by the rear zone.

In the case of the wearing article wherein the supporting sheet is elastically stretchable/contractible so that, even when the waist-hole of the pants is forcibly broadened by the wearer's waist, the supporting sheet is correspondingly stretched in the longitudinal direction and a contractile force of this supporting sheet causes the pad to be held in close contact with the wearer's skin. In this way, the article allows the pad to be reliably maintained in close contact with the wearer's skin. The intermediate section of the supporting sheet is spaced upward from the crotch region of the pants and this unique arrangement protects the rear zone of the pad interposed between the pants and the intermediate section of the supporting sheet from readily collapsing due to the presence of the supporting sheet and reliably eliminate an anxiety that urine once received by the rear zone might leak out through the opening.

DETAILED DESCRIPTION OF THE PREFERRED EMBODIMENTS

Details of a wearing article according to the present invention will be more fully understood from the description given hereunder with reference to the accompanying drawings.

Figure 1:
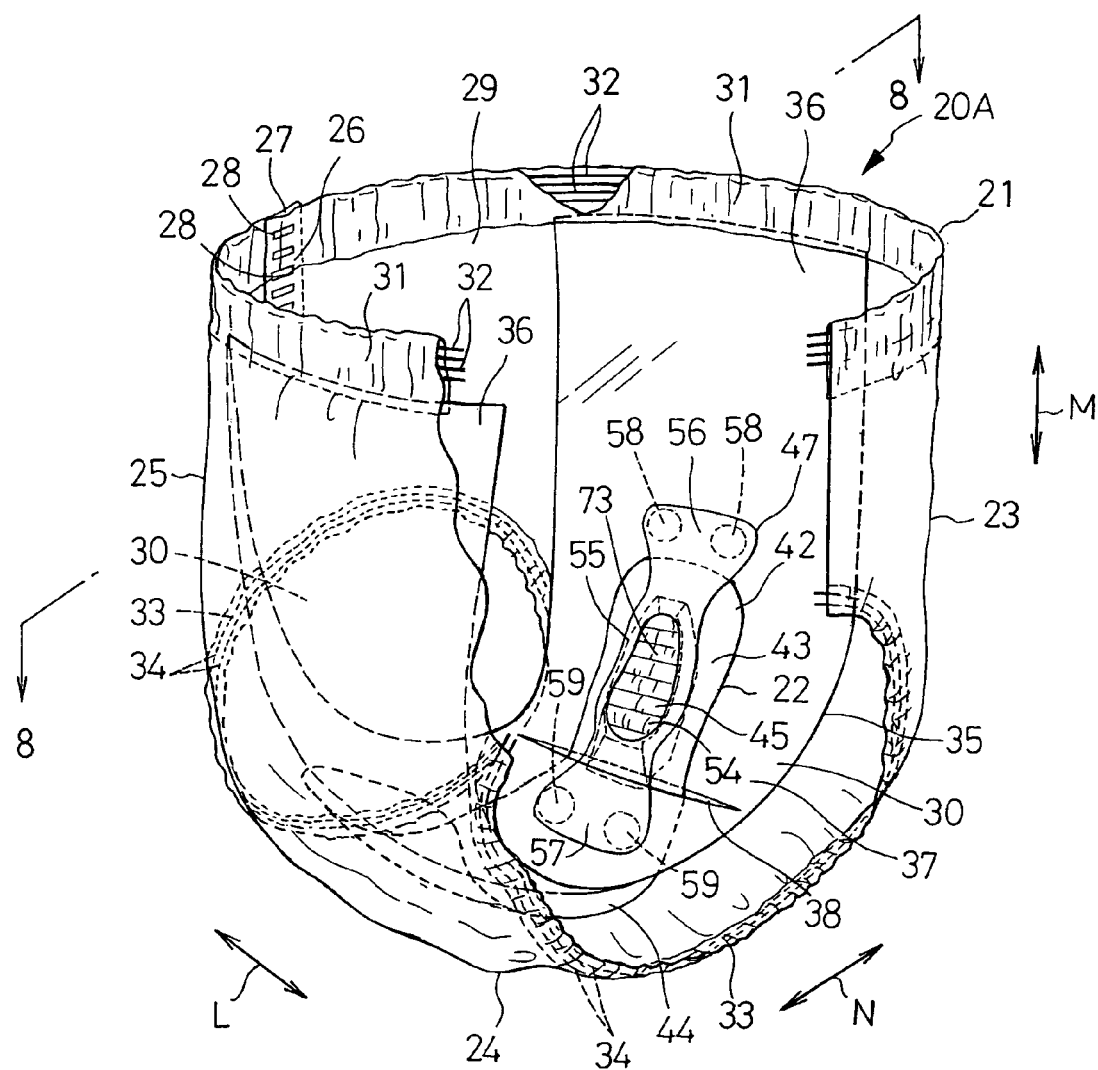
FIG. 1 is a perspective view showing a first embodiment of a wearing article according to the present invention with the pants partially broken away.
Figure 2:
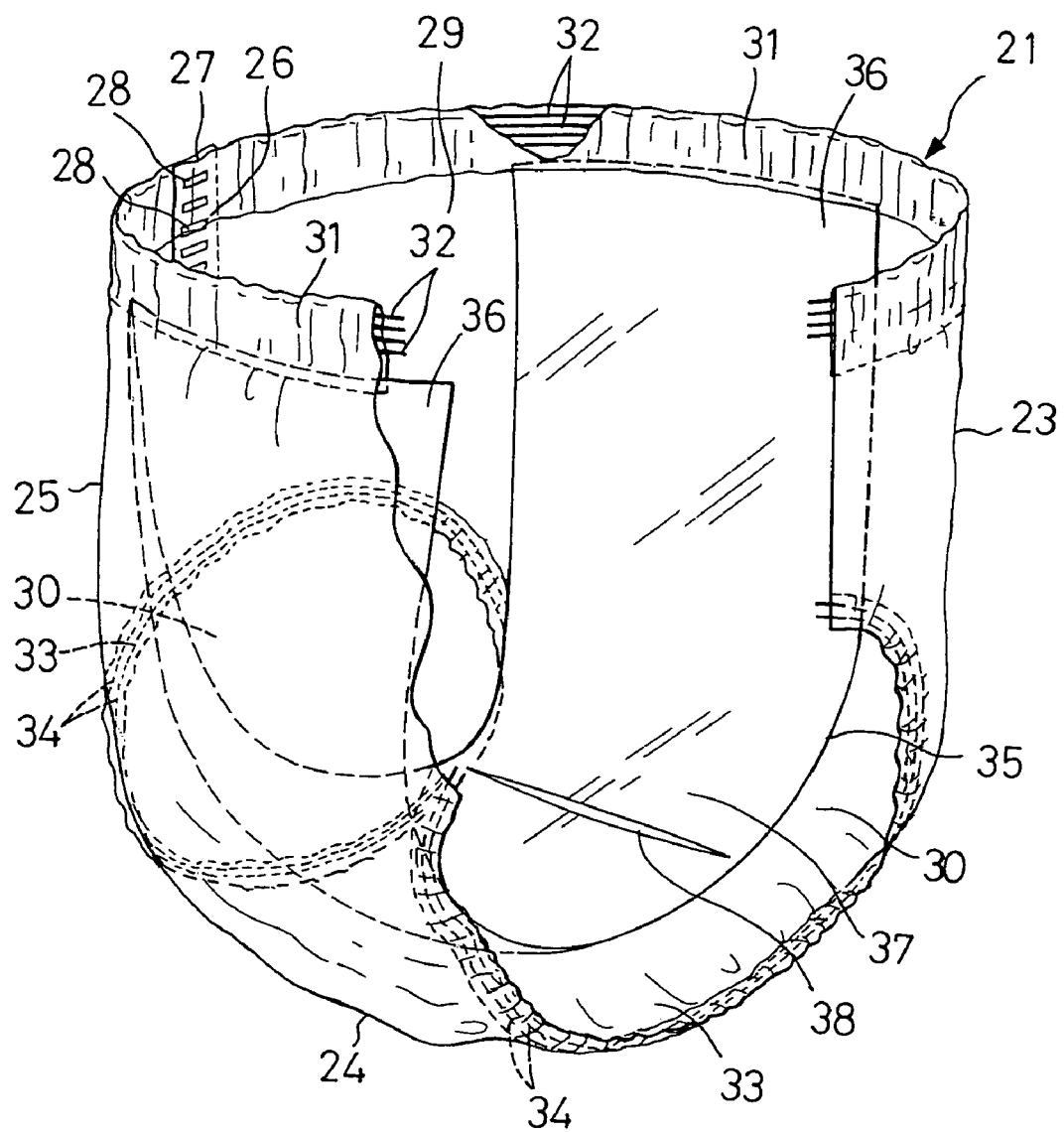
FIG. 2 is a perspective view showing the pants as partially broken away.

FIG. 1 is a perspective view showing a wearing article 20A with pants 21 partially broken away and FIG. 2 is a perspective view showing the pants 21 as partially broken away. Referring to FIG. 1, joined sheet 47 is fixed to a supporting sheet 35 and a body waste retaining pad 22 is attached to the pants 21 by means of the supporting sheet 35. FIG. 2 shows the pad 22 removed from the pants 21. The article 20A comprises the pants 21 and the body waste retaining pad 22 releasably attached to the inner side of the pants 21.

The pants 21 are made of a hydrophobic fibrous nonwoven fabric and has front and rear waist regions 23, 25 opposed to each other and a crotch region 24 extending between these two waist regions 23, 25. The front waist regions 23 has transversely opposite side edge zones 26 bonded to transversely opposite side edges 27 of the rear waist region 25 by means of a plurality of heat sealing spots 28 arranged intermittently along the side edge zones 26, 27. Thus, the pants 21 have a waist-hole 29 and a pair of leg-holes 30.

A waist-surrounding peripheral zone 31 of the pants 21 defining the waist-hole 29 and respective leg-surrounding peripheral zones 33 of the pants defining the respective leg-holes 30 are contractibily attached with a plurality of waist-surrounding elastic members and a plurality of leg-surrounding elastic members by means of adhesives (not shown), respectively. Inside the pants 21, a elongate supporting sheet 35 extends in the longitudinal direction between the front and rear waist regions 23, 25.

The supporting sheet 35 is made of a hydrophobic fibrous nonwoven fabric which is elastically stretchable and contractible. This supporting sheet 35 extends from the front and rear waist regions 23, 25 downward in the vertical direction so as to describe a circular arc. The supporting sheet 35 has opposite fixed end portions 36 fixed to the peripheral zone 31 of the front and rear waist regions 23, 25, a free intermediate section 37 extending between the fixed end portions 36. The free intermediate section 37 is not bonded to the pants 21 so as to be left free therefrom above the crotch region 24. The free intermediate section 37 is provided in its transversely middle zone with a slit (slot) 38 formed by cutting this middle zone in the transverse direction without extending to transversely opposite edges of this middle zone. The slit 38 is positioned in a longitudinally middle zone of the crotch region 24.

Figure 3:
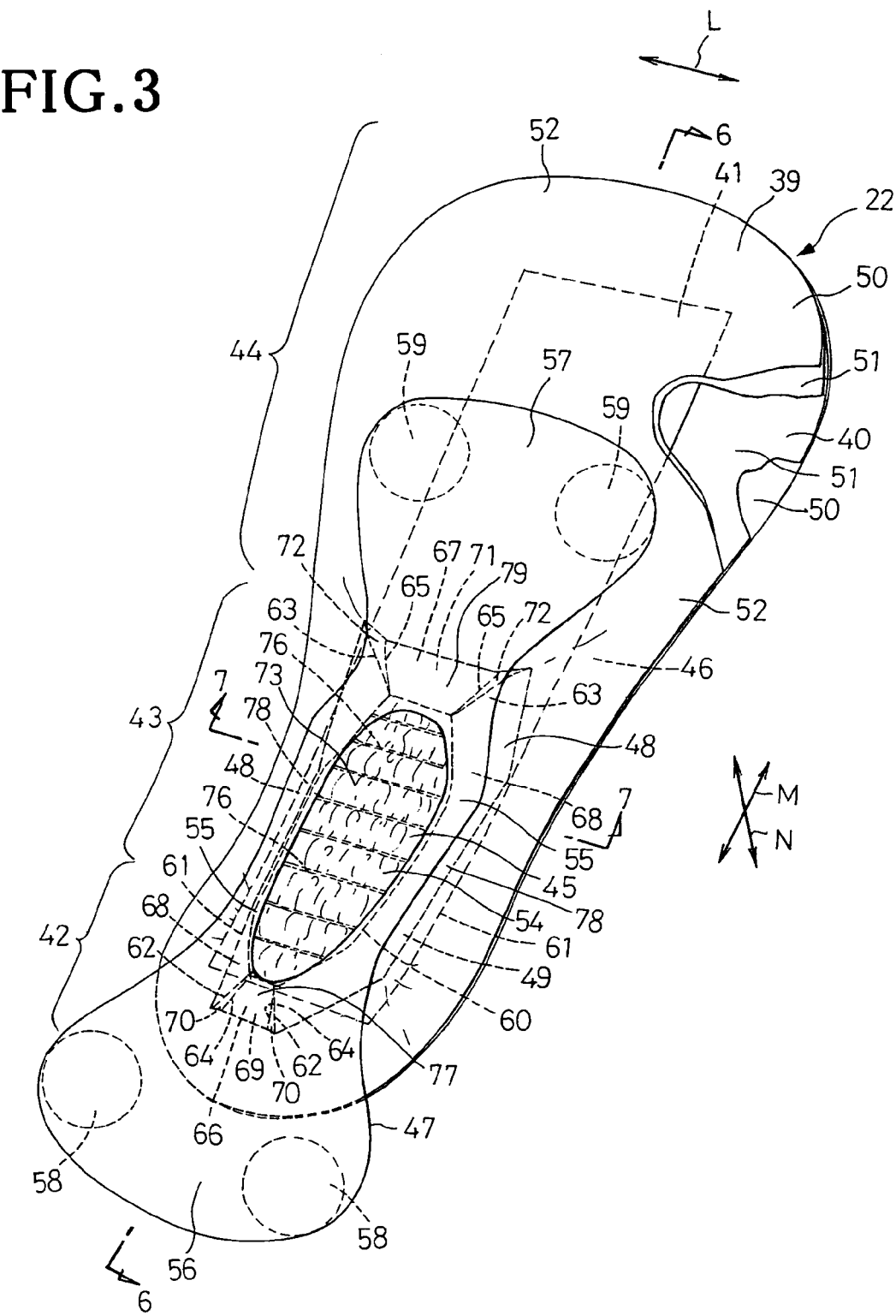
FIG. 3 is a perspective view showing the pad adapted to retain bodily waist as viewed from the side of the front waist region.
Figure 4:
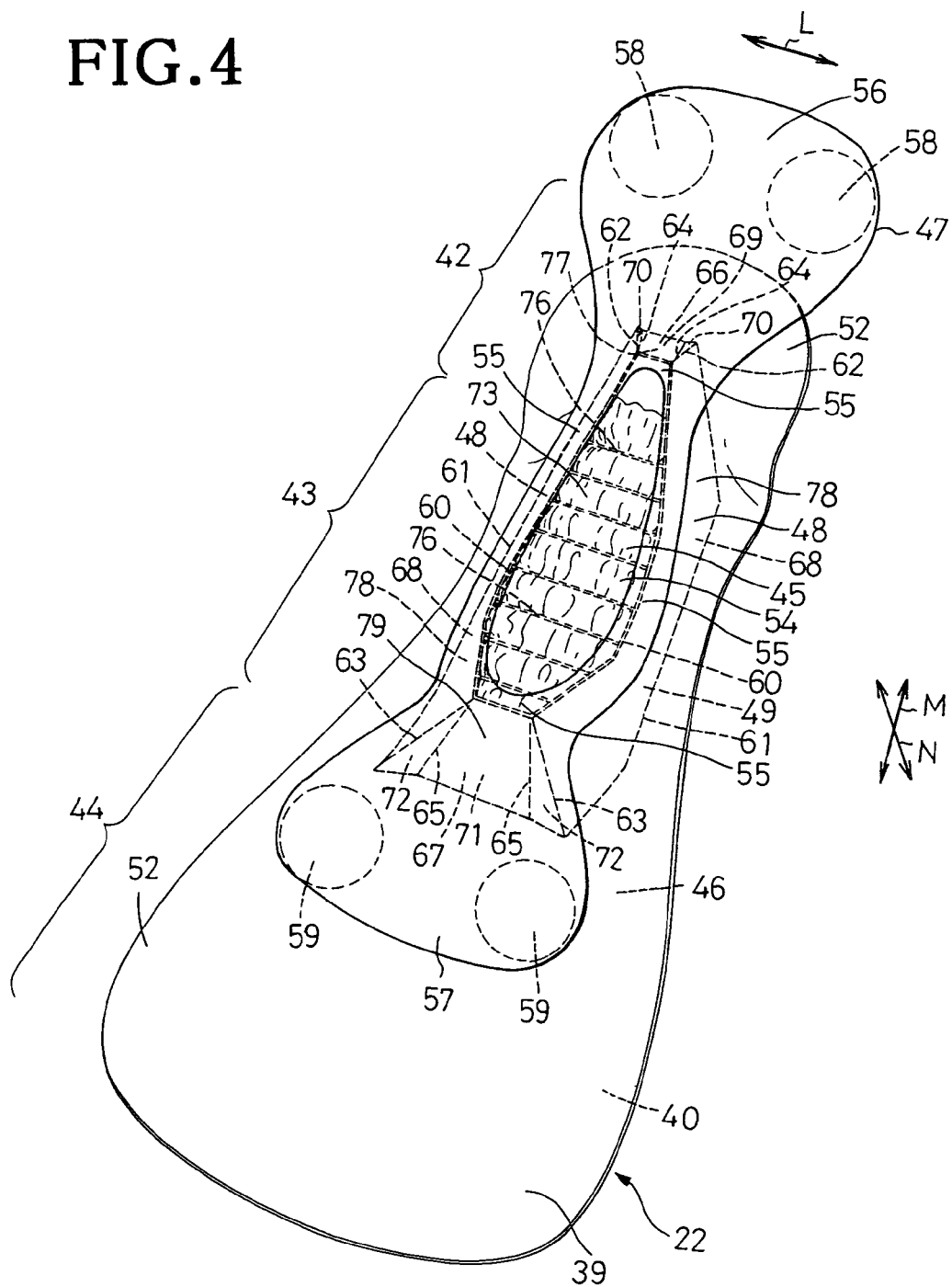
FIG. 4 is a partially cutaway perspective view showing the pad as viewed from the side of the rear waist region.
Figure 5:
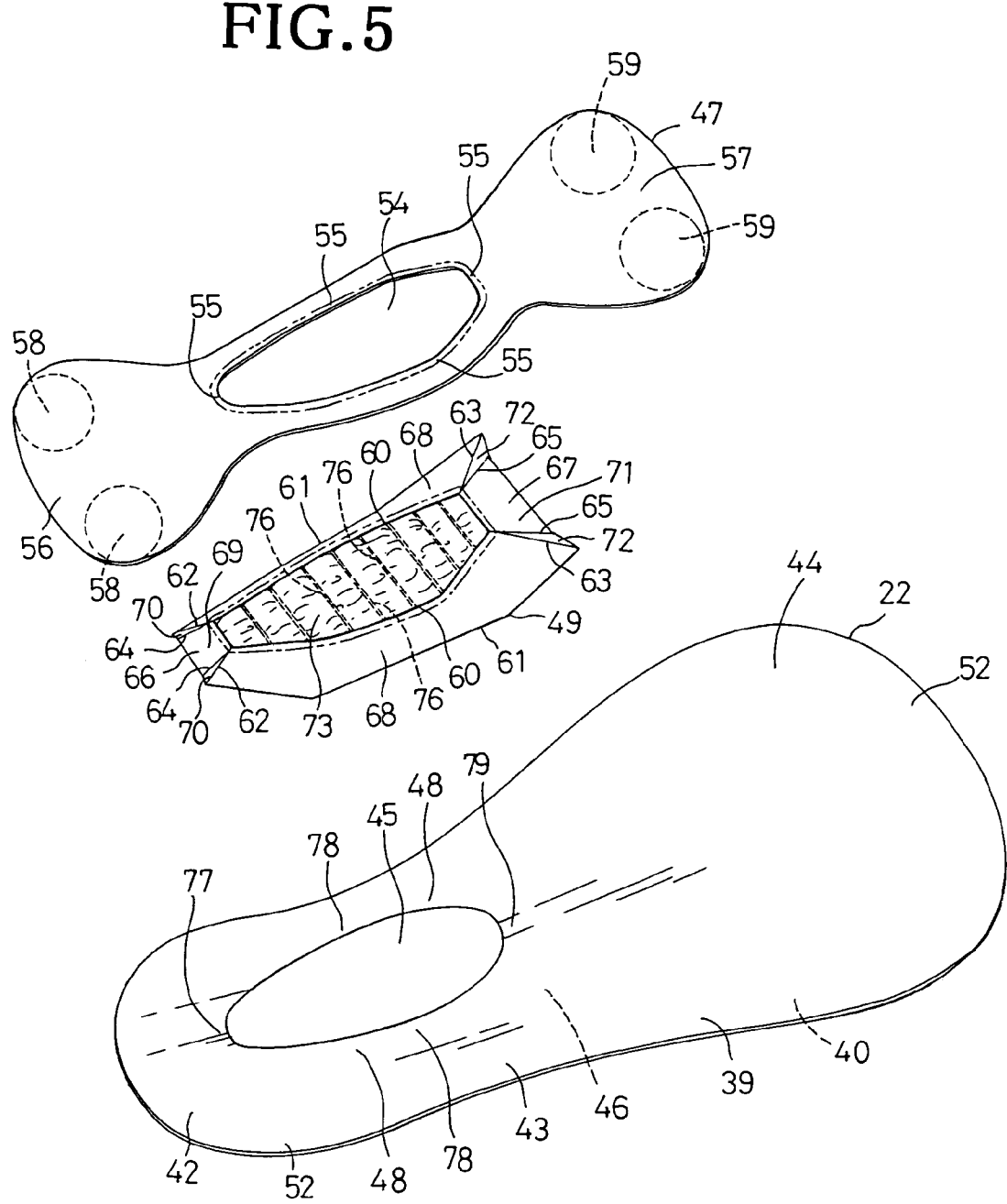
FIG. 5 is an exploded perspective view showing the joined sheet, the board and the pad separated one from another.
Figure 6:
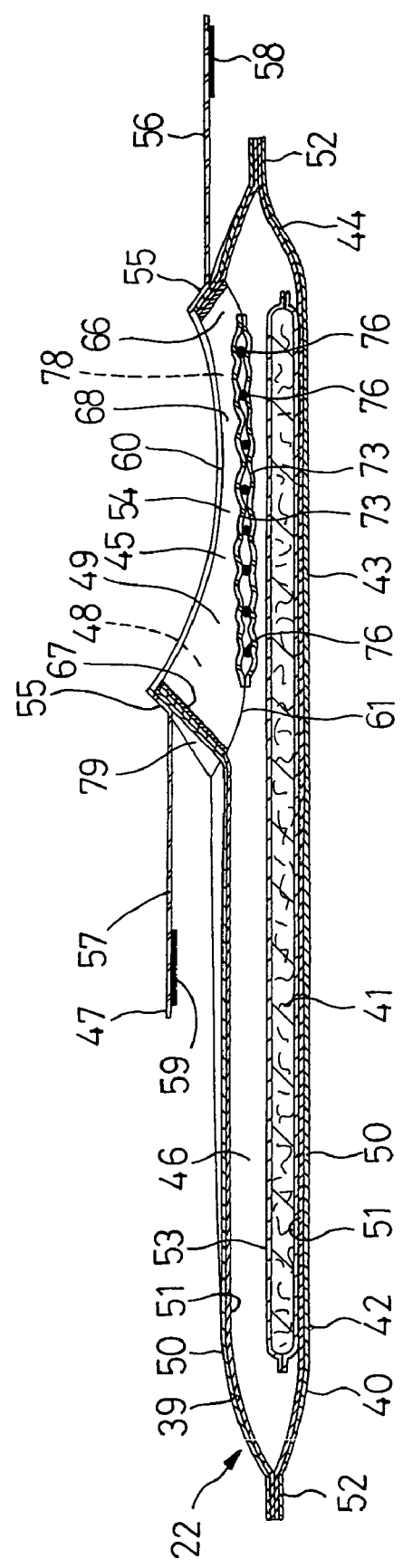
FIG. 6 is a sectional view taken along a line 6-6 in FIG. 4.
Figure 7:
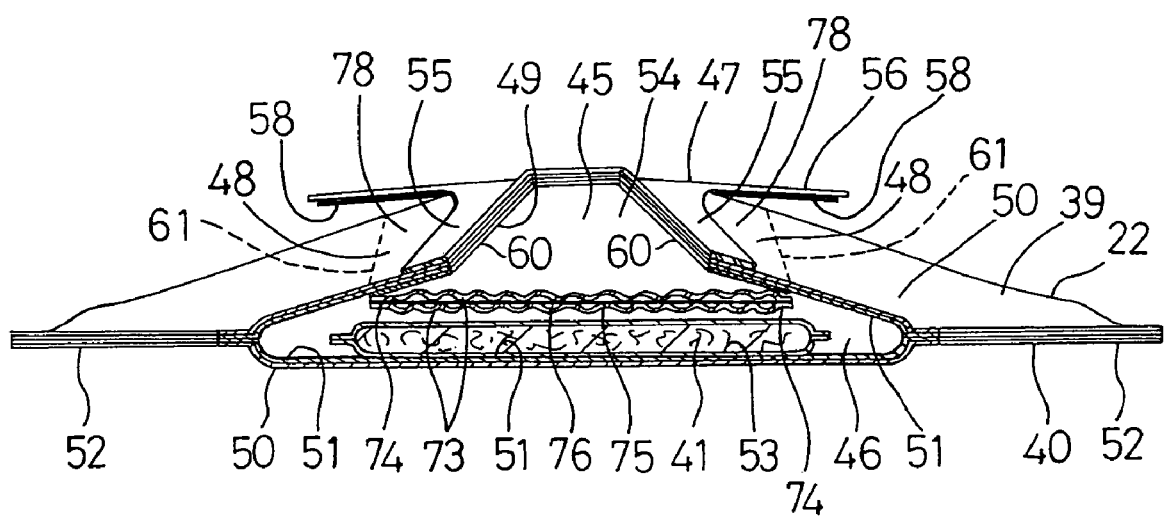
FIG. 7 is a sectional view taken along a line 7-7 in FIG. 4.

FIG. 3 is a perspective view showing the absorbent pad 22 adapted to retain bodily wastes as viewed from the side of the front waist region 42, FIG. 4 is a partially cutaway perspective view showing the pad 22 as viewed from the side of the rear waist region 44 and FIG. 5 is an exploded perspective view showing the joined sheet 47, the pad 22 and a board 49 separated one from another. FIGS. 6 and 7 are sectional views taken along lines 6-6 and 7-7, respectively, in FIG. 4.

The pad 22 comprises a liquid-impervious upper sheet 39 facing the wearer, a liquid-impervious lower sheet 40 facing away from the wearer and a liquid-absorbent core 41 interposed between these sheets 39, 40. The pad 22 has a front zone 42 and a rear zone 44 as viewed in the longitudinal direction and an intermediate zone 43 extending between these front and rear zones 42, 44. The pad 22 is formed with a first opening 45 which is relatively long in the longitudinal direction. This opening 45 extends through the appear sheet 39 and continuously extends in the front zone 42 and the intermediate zone 43 along transversely middle areas of these zones 42, 43. The upper sheet 39 and the lower sheet 40 define therebetween a space 46 adapted to contain bodily wastes having passed through the opening 45.

The joined sheet 47 is attached to the upper surface of the upper sheet 39 (i.e., the upper surface of the pad 22). The board 49 may be made of paper having a stiffness higher than those of the upper and lower sheets 39, 40 and is attached to the upper sheet 39 along a peripheral zone 48 defining the opening 45. Of the pad 22, the rear zone 44 has an area larger than those of the front zone 42 and the intermediate zone 43 so that the rear zone 44 defines a pouch-like shape which roundly widens rearward as viewed in the longitudinal direction of the pad 22. Thus the rear zone 44 has a bodily waste absorbing capacity higher than those of the front zone 42 and the intermediate zone 43.

Both the upper sheet 39 and the lower sheet 40 may be formed from a composite sheet composed of a hydrophobic fibrous nonwoven fabric 50 and a breathable liquid-impervious plastic film 51 laminated together. Therefore the respective upper and lower sheets 39, 40 as well as their laminate have a stiffness lower than that of the board 49. Preferably, peripheral zones 52 of the upper and lower sheets 39, 40 extending outward beyond the periphery of the core 41 are water-tightly bonded to each other.

The core 41 extends over the front zone 42, the rear zone 44 and the intermediate zone 43 and bonded to the inner surface of the lower sheet 40. The core 41 is a mixture of particulate or fibrous super-absorbent polymers and fluff pulp fibers a mixture of particulate or fibrous super-absorbent polymers, fluff pulp fibers and thermoplastic synthetic resin fibers compressed to a desired thickness. The core 41 is entirely wrapped with a liquid-pervious sheet 53 such as a tissue paper or hydrophilic fibrous nonwoven fabric in order to prevent the core 41 from getting out of its desired shape.

The joined sheet 47 may be made of a urethane foam material. The joined sheet 47 is formed with a second opening 54 which extends through the thickness of the sheet 47 and is elongate in the longitudinal direction. The second opening 54 is generally the same as the first opening 45 in shape as well as in size and contiguous to the first opening 45. The joined sheet 47 has a proximal inner peripheral zone 55 bonded to the upper surface of the upper sheet 39 along the peripheral zone 48 defining the first opening 45, a distal front zone 56 extending forward from the front zone 42 of the pad 22 and a distal rear zone 57 extending in the rear zone 44 of the pad 22. Both the distal front and rear zones 56, 57 are not bonded to the upper sheet 39. The distal front zone 56 is provided on its lower surfaces with circular hook members 58 as fastener means spaced from each other in the transverse direction and bonded thereto. The distal rear zone 57 also is provided on its lower surface with circular hook members 59 as fastener means spaced from each other in the transversely direction and bonded thereto.

The board 49 circularly extends along the opening's peripheral zone 48 so as to surround the opening 45. The board 49 has an inner periphery 60 lying adjacent to the opening 45 and an outer periphery 61 opposed to the inner periphery 60. The board 49 has its upper surface bonded to the upper surface of the upper sheet 39. The board 49 is folded along a pair of first folding guides 62, a pair of second folding guides 63, a pair of third folding guides 64 and a pair of fourth folding guides 65.

The first folding guides 62 are provided in front as viewed in the longitudinal direction of the opening's peripheral zone 48 and extend between the inner periphery 60 and the outer periphery 61 of the board 49. The first folding guides 62 are spaced from and opposed to each other in the transverse direction so that a dimension by which these folding guides 62 are spaced from each other gradually widens from the inner periphery 60 toward the outer periphery 61 of the board 49. The second folding guides 63 are provided at the rear as viewed in the longitudinal direction of the opening's peripheral zone 48 and extend between the inner periphery 60 and the outer periphery 61 of the board 49. The second folding guides 63 are spaced from and opposed to each other in the transverse direction so that a dimension by which these folding guides 63 are spaced from each other gradually widens from the inner periphery 60 toward the outer periphery 61 of the board 49. The board 49 is folded (specifically accordion-folded) along the first folding guides 62 and the second folding guides 63 so that the board 49 may become convex outward with respect to the opening's peripheral zone 48.

The third folding guides 64 are provided between the pair of first folding guides 62 and branched on the inner periphery 60 of the board 49 from the first folding guides 62 so as to extend to the outer periphery 61 of the board 49. The third folding guides 64 are spaced from and opposed to each other in the transverse direction so that a dimension by which these folding guides 64 are spaced from each other gradually widens from the inner periphery 60 toward the outer periphery 61 of the board 49. The fourth folding guides 65 are provided between the pair of second folding guides 63 and branched on the inner periphery 60 of the board 49 from the second folding guides 63 so as to extend to the outer periphery 61 of the board 49. The fourth folding guides 65 are spaced from and opposed to each other in the transverse direction so that a dimension by which these folding guides 65 are spaced from the second folding guides 63 gradually widens from the inner periphery 60 toward the outer periphery 61 of the board 49. The board 49 is folded (specifically accordion-folded) along the third folding guides 64 and the fourth folding guides 65 so that the board 49 may become convex inward with respective to the opening's peripheral zone 48.

The board 49 is substantially defined by a front wall lying in front with respect to the longitudinal direction of the opening's peripheral zone 48 and extending between the pair of first folding guides 62, a rear wall 67 lying at the rear with respect to the longitudinal direction of the opening's peripheral zone 480 and extending between the pair of second folding guides 63 and transversely opposite side walls 68 being contiguous to the front and rear walls 66, 67 and extending between the first and second folding guides 62, 63. Of the board 49, each of the side walls 68 is tapered from the rear wall 67 toward the front wall 66 so that the rear wall 67 has an area larger than that of the front wall 66. The front wall 66 is divided into a trapezoidal middle segment 69 extending between the pair of third folding guides 64 so as to be concave rearward as viewed in the longitudinal direction of the opening's peripheral zone 48 and triangular lateral segments 70 respectively extending between the first and third folding guides 62, 64 so as to be opposed to the respective side walls 68. The rear wall 67 is divided into a trapezoidal middle segment 71 extending between the pair of fourth folding guides 65 so as to be concave forward as viewed in the longitudinal direction of the opening's peripheral zone 48 and triangular lateral segments 72 respectively extending between the second and fourth folding guides 63, 65 so as to be opposed to the respective side walls 67.

Water-pervious sheets 73 is stretched in the transverse direction and attached in this state to the transversely opposite side walls 67 of the board 49 along the outer periphery 61. The water-pervious sheets 73 extending in the space 46 immediately below the opening 45 has transversely opposite fixed side edges 74 bonded to the outer periphery 61 of the respective side walls 67 an intermediate segment 75 extending between these fixed side edges 74. The water-pervious sheets 73 is provided therebetween with a plurality of stretchable/contractible elastic members 76 contractibly attached thereto wherein these elastic members 76 are spaced one from another by a given dimension in the longitudinal direction and extending in the transverse direction. Specifically, these elastic members 76 are stretched at a given ratio in the transverse direction and bonded in this state to the sheets 73. The side walls 68 of the board 49 are normally biased by a contractile force of the elastic members 76 to be drawn inward as viewed in the transverse direction of the pad 22. Of the board 49, the front and rear walls 66, 67 opposed to each other slant downward from the opening 45 toward the lower sheet 40 and the opposite side walls 68 also slant downward from the opening 45 toward the lower sheet 40. In this manner, the board 49 has a three-dimensional shape which is convex upward to the apex defined by the opening 45 above the lower sheet 40.

The opening's peripheral zone 48 is divided into a front region 77 extending in the front wall 66 of the board 49, transversely opposite lateral regions 78 extending in the respective side walls 68 of the board 49 and a rear region 79 extending in the rear wall 67 of the board 49. Of the opening's peripheral zone 48, the lateral regions 78 are tapered from the rear region 79 toward the front region 77 and the rear region 79 has an area larger than that of the front region 77. The front region 77 is divided into a middle segment extending in the middle segment 69 of the front wall 66 and transversely opposite lateral segments extending in the respective lateral segments 72 of the front wall 66. The rear region 79 is divided into a middle segment extending in the middle segment 71 of the rear wall 67 and transversely opposite lateral segments extending in the respective lateral segments 72 of the rear wall 67. Of the opening's peripheral zone 48, the front and rear regions 77, 79 opposed to each other slant outward from the opening 45 toward the lower sheet 40 as the front and rear walls 66, 67 of the board 49 slant outward. The transversely opposite lateral segments 78 also slant outward toward the lower sheet 40 as the transversely opposite side walls 68 of the board 49 slant outward. In this manner, the opening's peripheral zone 48 is deformed in conformity with the front and rear walls 66, 67 as well as the side walls 68 of the board 49 and has the corresponding three-dimensional shape which is convex upward above the lower sheet 40.

Figure 8:
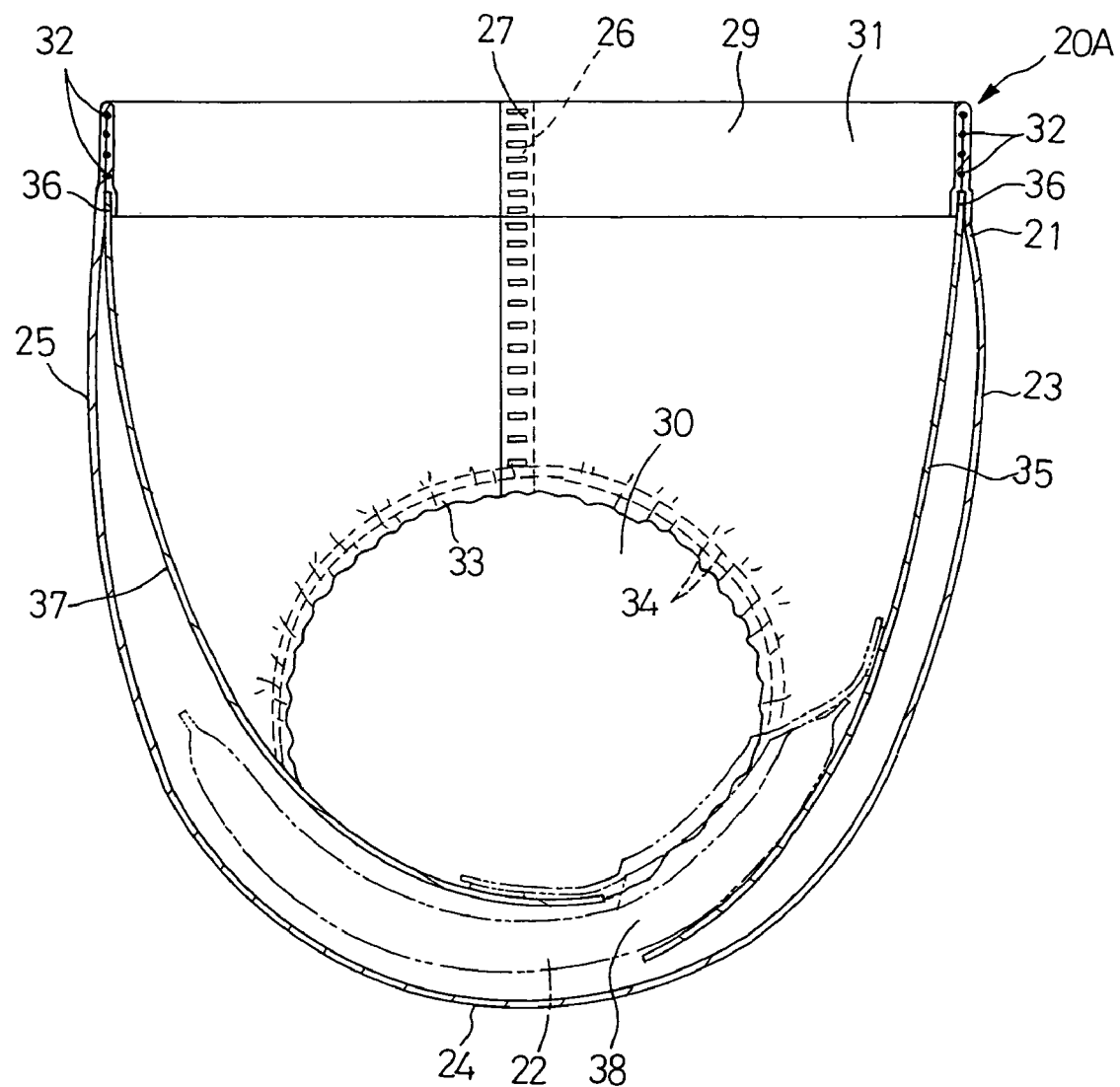
FIG. 8 is a sectional view taken along a line 8-8 in FIG. 1.
Figure 9:
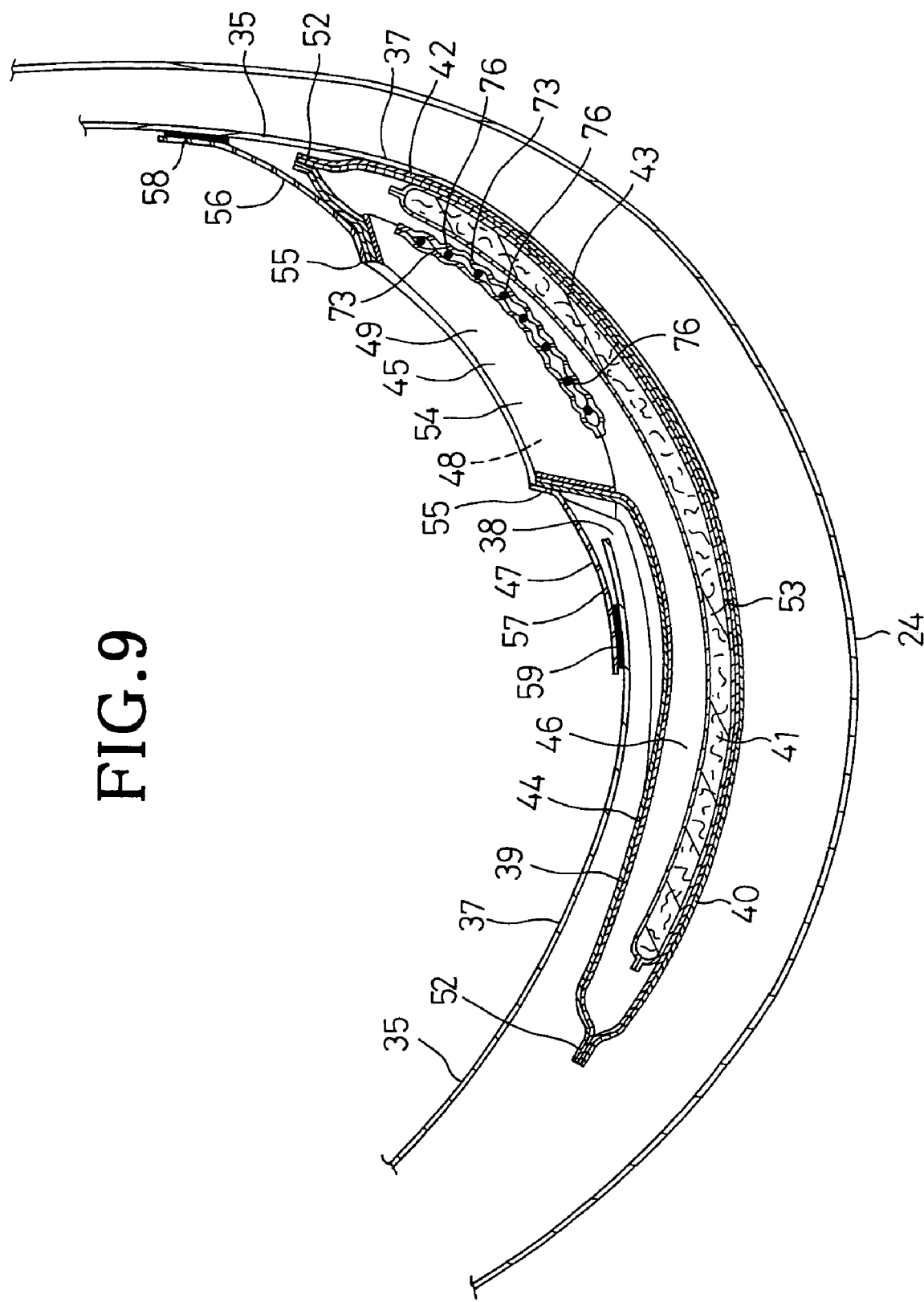
FIG. 9 is a view showing a part of FIG. 8 in an enlarged scale.

FIG. 8 is a sectional view taken along the line 8-8 in FIG. 1 and FIG. 9 is a view showing a part of FIG. 8 in an enlarged scale. In FIG. 8, the pad 22 is schematically indicated by a chain double-dashed line. To attach the pad 22 to the supporting sheet 35, the front zone 42 and the intermediate zone 43 of the pad 22 are placed upon the upper surface of the supporting sheet 35, the rear zone 44 of the pad 22 is inserted toward the side of the rear waist region 25 of the pants 21 through the slit 38 and the rear zone 44 is interposed between the pants 21 and the supporting sheet 35. Then the lower surfaces of the distal front and rear zones 56, 57 of the joined sheet 47 are fastened to the upper surface of the supporting sheet 35 by means of the hook members 58. In this way, the front zone 42 and the intermediate zone 43 of the pad 22 are secured to the supporting sheet 35. The rear zone 44 of the pad 22 is interposed between the pants 21 and the supporting sheet 35 without being secured to the supporting sheet 35. The front zone 42 and the intermediate zone 43 extend over a generally front half of the crotch region 24 of the pants 21 and the rear zone 44 extends over a generally rear half of the crotch region 24 of the pants 21. Urine discharged during use of the article 20A is guided through the openings 45, 54 into the space 46 of the pad 22, and absorbed and retained by the core 41.

The front zone 42 and the intermediate zone 43 of the pad 22 are secured to the upper surface of the supporting sheet 35 as the pad 22 is attached to the pants 21 by means of the supporting sheet 35. It is ensured thereby that a movement of the pants 21 is not transmitted directly to the pad 22 and therefore the pad 22 does not follow the wearer's movement even if the pants 21 moves as the wearer moves. The pad 22 does not slip down even if the pants 21 slips down from the proper position around the wearer's body. Thus the pad 22 is reliably maintained in close contact with the wearer's skin and it is unlikely that urine might be discharged outside the pad 22. In the article 20A, the rear zone 44 of the pad 22 is interposed between the pants 21 and the supporting sheet 35 so that the rear zone 44 of the pad 22 can be protected from readily collapsing and urine once absorbed by the rear zone 44 never leaks out through the opening 45 to the outside of the pad 22 even when a body pressure of the wearer is exerted on the article 20A. The article 20A allows the pad 22 having absorbed urine therein to be released from the pants 21 for disposal. In this manner, the pad 22 alone can be exchanged with a new one and the pants 21 can be reused repetitively.

The rear zone 44 of the pad 22 has a pouch-like shape which gradually widens as the rear zone 44 roundly extends rearward in the longitudinal direction and correspondingly the rear zone 44 roundly achieves an absorption capacity higher than those achieved by both the front zone 42 and the intermediate zone 43 of the pad 22. Even if a relatively large amount of urine is discharged during use of the article 20A, this amount of urine can be completely received by the rear zone 44. Urine received by the pad 22 in this manner is absorbed and retained by the core 41 and there is unlikely that urine once contained in the space 46 might leak out through the opening 45.

The supporting sheet 35 is elastically stretchable/contractible so that, even when the waist-hole 29 of the pants 21 is forcibly broadened by the wearer's waist, the supporting sheet 35 is correspondingly stretched in the longitudinal direction and a contractile force of this supporting sheet 35 causes the pad 22 to be held in close contact with the wearer's skin. In this way, the article 20A allows the pad 22 to be reliably maintained in close contact with the wearer's skin. The intermediate section 37 of the supporting sheet 35 is spaced upward from the crotch region 24 of the pants 21 and this unique arrangement protects the rear zone 44 of the pad 22 interposed between the pants 21 and the intermediate section 37 of the supporting sheet 35 from readily collapsing due to the presence of the supporting sheet 35 and reliably eliminate an anxiety that urine once received by the rear zone 44 might leak out through the opening 45.

Of the opening's peripheral zone 48 of the upper sheet 39 which is convex upward above the lower sheet 40, the front and rear regions 77, 78 as well as the lateral regions 79 form the barriers against urine and eliminate the anxiety that urine might flow beyond the opening's peripheral zone 48 and urine once contained in the space 46 might flow back through the opening 45 toward the outside of the pad 22. The board 49 attached to the opening's peripheral zone 48 of the upper sheet 39 has a stiffness sufficiently higher than those of the upper and lower sheets 39, 40 to maintain the three-dimensional shape of the opening's peripheral zone 48 even if a slight pressure is exerted on the pad 22 in the thickness direction. In this way, the opening's peripheral zone 48 does not readily collapse and the opening's peripheral zone 48 as the barrier against urine is not defunctionalized.

The lateral segments 70 in the front wall 66 of the board 49 extending between the first and third folding guides 62, 64 cooperate with the side walls 68 to support a pressure exerted on the pad 22 in the thickness direction. Similarly, the lateral segments 72 in the rear wall 67 of the board 49 extending between the second and fourth folding guides 63, 65 cooperate with the side walls 68 to support such pressure exerted on the pad 22 in the thickness direction. In this way, a buckling strength of the board 49 against the pressure exerted on the pad 22 in the thickness direction is sufficiently improved to ensure that the opening's peripheral zone 48 does not readily collapse and the three-dimensional shape of the opening's peripheral zone 48 is reliably held by the board 49.

The contractile force of the elastic members 76 causes the side walls 68 of the board 49 to be drawn inward toward each other as viewed in the transverse direction of the pad 22 and thereby the three-dimensional shape of the board 49 to be reliably maintained. The board 49 cooperates with the elastic members 76 to reliably maintain the opening's peripheral zone 48 in its three-dimensional shape which is convex upward above the lower sheet 40. Even if the opening's peripheral zone 48 collapses under a high pressure exerted on the pad 22 in the thickness direction and consequently the board 49 is flattened, the contractile force of the elastic members 76 causes the board 49 to restore its three-dimensional shape as soon as such pressure is relieved, and consequently the opening's peripheral zone 48 also restores its three-dimensional shape which is convex upward above the lower sheet 40. The side walls 68 of the board 49 are tapered from the rear wall 67 toward the front wall 66 and the rear wall 67 has an area larger than that of the front wall 66. This unique configuration ensures that the front wall 66 as well as the side walls 68 of the board 49 is neatly received in the wearer's crotch region without suffering from uncomfortable bulkiness feeling due to the presence of the opening's peripheral zone 48.

The board 49 has a stiffness value in a range of 2 to 40 mN·m. If the stiffness value of the board 49 is less than 2 mN·m, the board 49 will readily collapse under a pressure exerted on the board 49 in the thickness direction of the pad 22 and the opening's peripheral zone 48 can not be maintained in its desired three-dimensional shape which is convex upward above the lower sheet 40. If the stiffness value of the board 49 exceeds 40 mN·m, the opening's peripheral zone 48 being in contact with the wearer's skin during use of the article 20A will uncomfortably irritate the wearer's skin. The stiffness value of the board 49 was measured in compliance with Taber's stiffness tester method (JIS P 8125).

(1) The same material as the board 49 used for the pad 22 was cut to obtain samples for measurement each having a longitudinal dimension of 50 mm and a transverse dimension of 25 mm. Taber's stiffness tester manufactured by YASUDA SEIKI SEISAKUSHO, LTD. in Japan was used to measure stiffness values of the respective samples in the longitudinal direction as well as in the transverse direction.
(2) The measurement was conducted in pursuance of steps as follow: (a) a thickness (A) of the sample is measured; (b) the sample is loosely pinched so that the sample is merely in contact with a (downside) chuck of the tester at a center thereof; (c) a sum of clearances between both surfaces of the sample and a pair of support rollers is adjusted to (A)×0.80(mm); (d) auxiliary weight ½ is loaded on; and (e) the sample is rotated in both directions until the scale of flexion angle 15° falls into line with central scale of a pendulum and divisions on the tester scale at this moment are read. A value read on the left side of the tester scale is represented by (B) and a value read on the right side of the tester scale is represented by (C).
(3) The stiffness value of the sample was calculated from an equation of equation: stiffness value (N·cm)=((B)+(C))/2×(auxiliary weight modulus)/1000×9.807. The stiffness value of the sample calculated was in a range of 2 to 40 mL in the longitudinal direction as well as in the transverse direction. The stiffness value of the sample was determined as the stiffness value of the board 49.

The elastic members 76 attached to the water-pervious sheets 73 have a tensile stretch stress in a range of 0.01 to 1.5N. The term "tensile stress of the elastic members 76" as used herein is the tensile stress exhibited by each of these elastic members 76. If the tensile stress of the elastic member 76 is less than 0.01N, a contractile force of the elastic member 76 will be insufficient to draw the side walls 68 toward each other in the transverse direction of the pad 22 by a desired dimension. Consequently, it may be impossible for the board 49 to restore its initial three-dimensional shape in which the opening's peripheral zone 48 is convex upward above the lower sheet 40. If the tensile stress of the elastic member 76 exceeds 1.5N, the side walls 68 of the board 49 will be excessively drawn toward each other in the transverse direction of the pad 22 until these side walls 68 come in contact with each other and the opening 45 is closed. The tensile stress of the elastic member 76 was measured by a method as follows:
(1) The same material as the elastic members 76 attached to the water-pervious sheets 73 was prepared as (a single) sample for measurement. For measurement of the tensile stress, the tensile tester manufactured by SHIMADZU CORPORATION in Japan was used.
(2) The measurement was conducted in pursuance of the steps as follow: longitudinally opposite ends of the sample were clamped by respective chucks of the tester (a dimension over which each end was clamped by the chuck: about 10 mm; a length dimension of the sample measured between the chucks: about 100 mm). The sample was stretched in the longitudinal direction at a rate of 100 mm/min and, after the sample had been stretched by 300%, the tension was relieved. The sample was stretched again in the longitudinal direction at a rate of 100 mm/min and a force exerted on the tester at this moment was measured. "The sample was stretched by 200%" as used here means that, for example, the sample has a dimension of 100 mm as measured between the chucks was stretched to 100 mm×2.0=200 mm. The tensile stress of the sample in a range of 0.01 to 1.5N was determined as the tensile stress exhibited by each of the elastic members 76.

Figure 10:
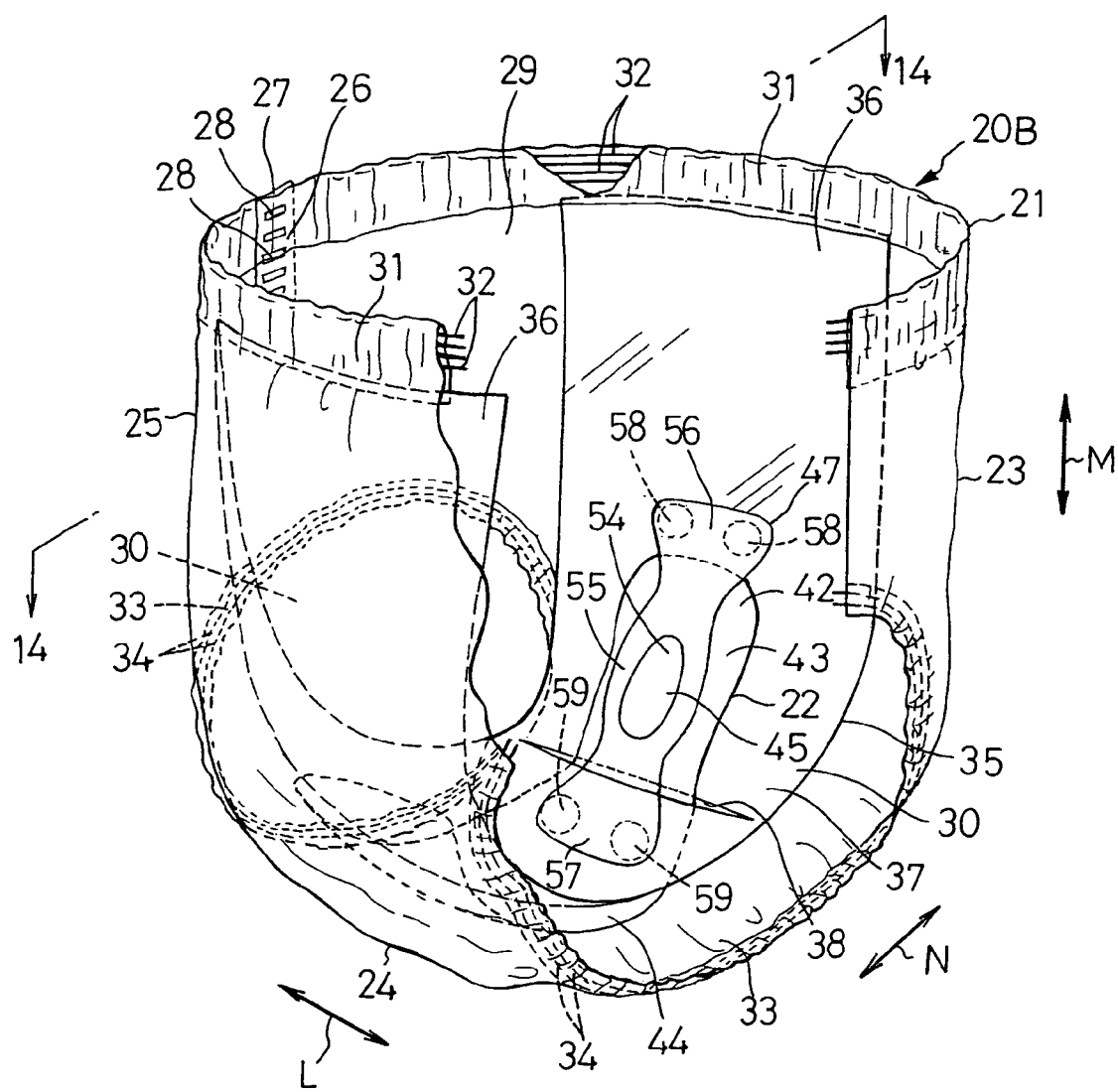
FIG. 10 is a perspective view showing a second preferred embodiment of the wearing article according to the present invention with the pants partially broken away.
Figure 11:
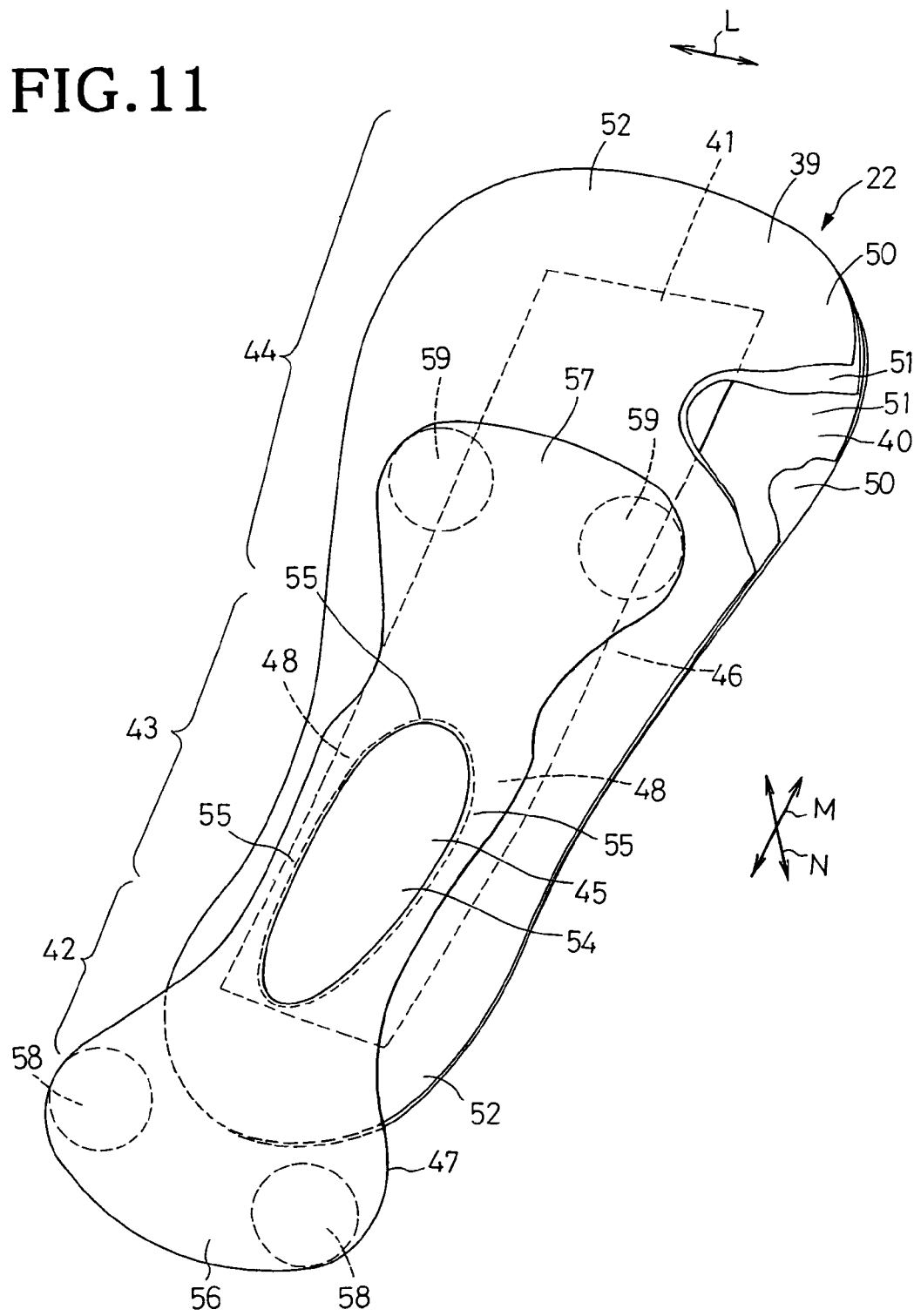
FIG. 11 is a partially cutaway perspective view showing the pad in this preferred embodiment adapted to retain bodily waist as viewed from the side of the front waist region.
Figure 12:
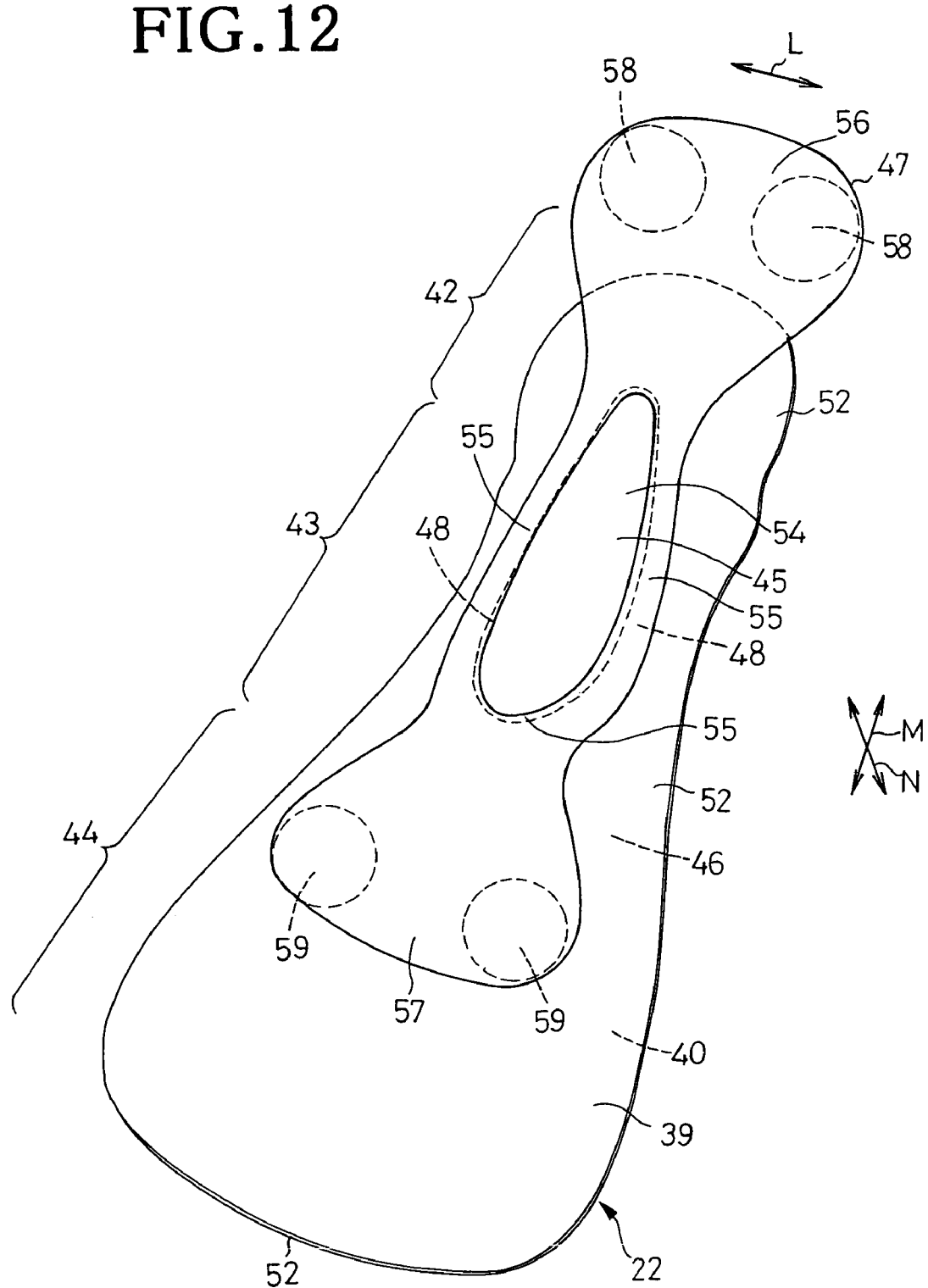
FIG. 12 is a perspective view showing the pants in this preferred embodiment as viewed from the side of the rear waist region.
Figure 13:
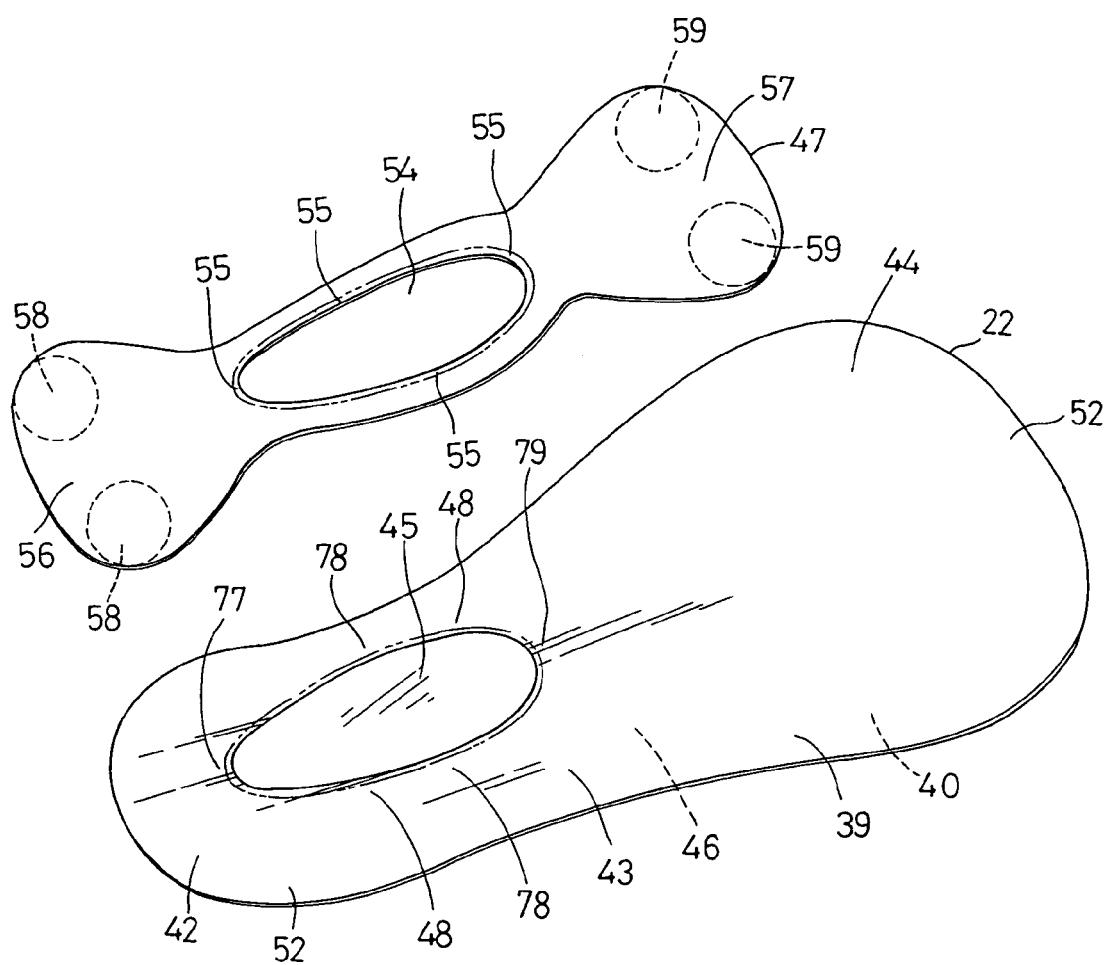
FIG. 13 is an exploded perspective view showing the pad and the joined sheet separated from each other.
Figure 14:
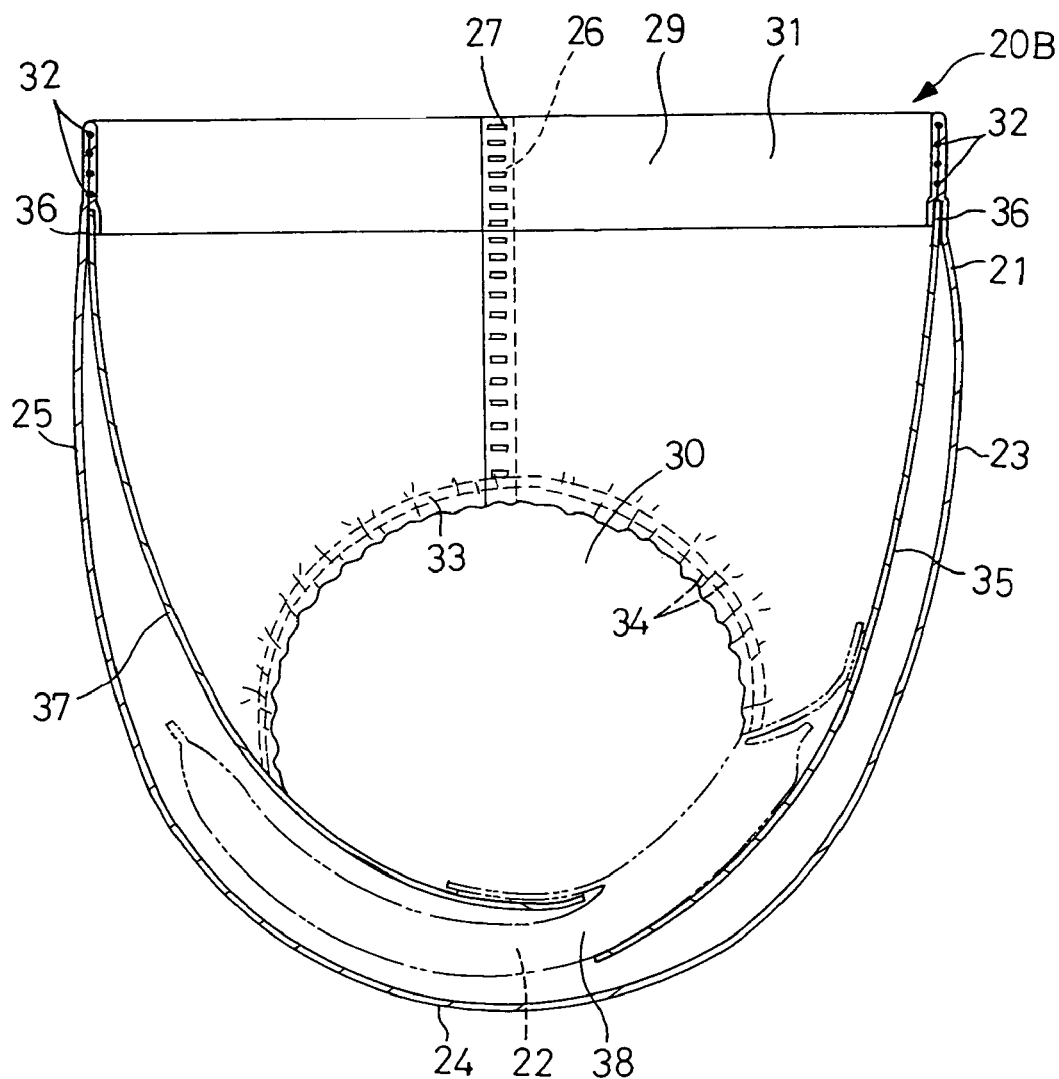
FIG. 14 is a sectional view taken along the line 14-14 in FIG. 10.
Figure 15:
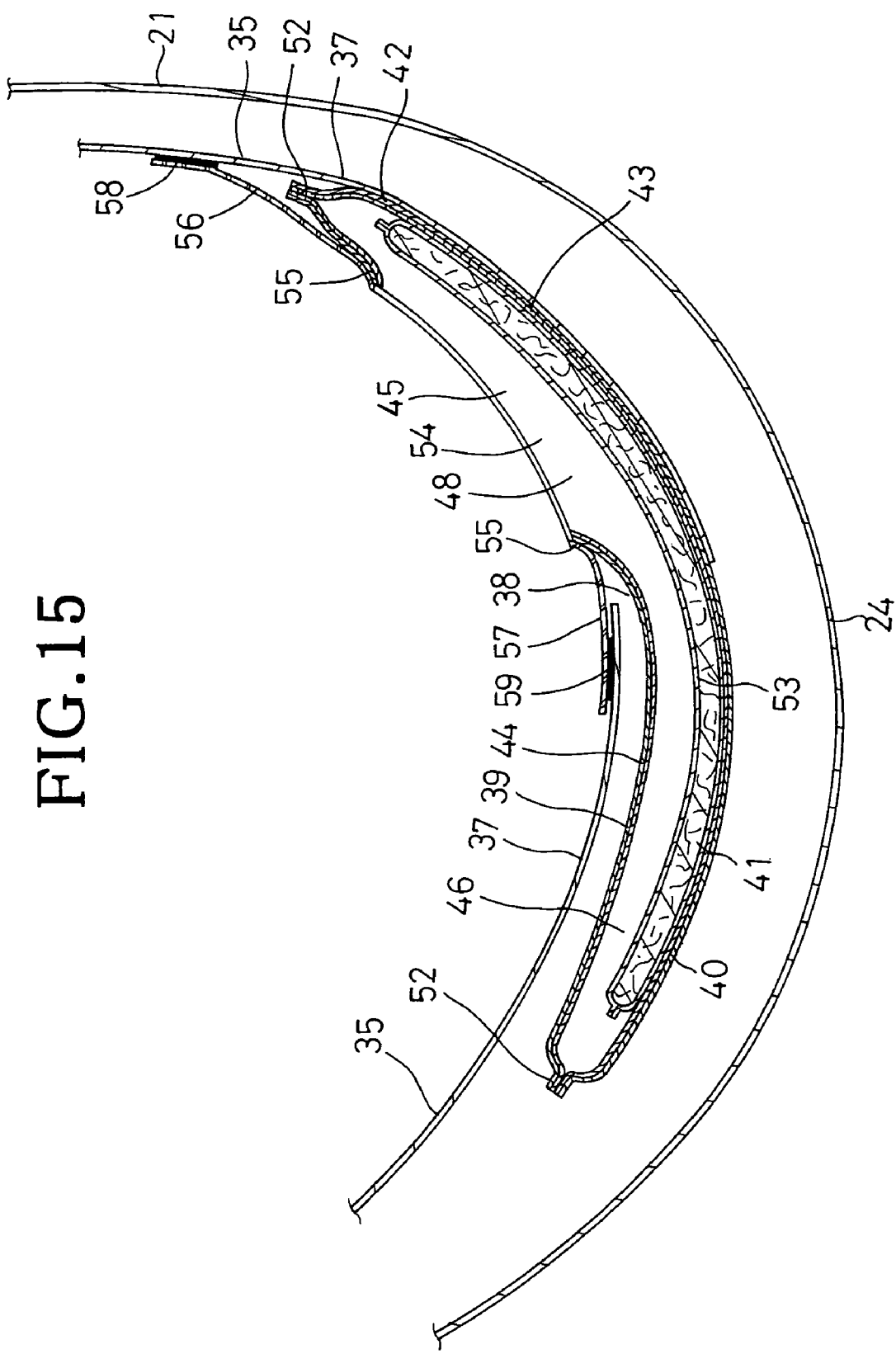
FIG. 15 is a view showing a part of FIG. 14 in an enlarged scale.

FIG. 10 is a perspective view showing a wearing article 20B as another preferred embodiment of the present invention with the pants 21 partially broken away, FIG. 11 is a partially cutaway perspective view showing the pad 22 in this preferred embodiment adapted to retain bodily waists as viewed from the side of the front waist region 42, FIG. 12 is a perspective view showing the pad 22 as viewed from the side of the rear waist region 44 and FIG. 13 is an exploded perspective view showing the pad 22 and the joined sheet 47 separated from each other. FIG. 14 is a sectional view taken along the line 14-14 in FIG. 10 and FIG. 15 is a view showing a part of FIG. 14 in an enlarged scale. In FIG. 14, the pad 22 is schematically indicated by a chain double-dashed line. The article 20B comprises the pants 21 and the body waste absorbent pad 22 releasable attached to the inner side of the pants 21. The pants 21, the pad 22 except for a part thereof, the supporting sheet 35 and the joined sheet 47 are identical to those shown in FIGS. 1 to 9 and designated by the same reference numerals as those in FIGS. 1 to 9. Therefore, duplicate description will be avoided here with respect to these pants 21, pad 22, supporting sheet 35 and joined sheet 47. In the article, the pad is not provided with the water-pervious sheets 73 and the elastic members 76 unlike the article 20A shown in FIGS. 1 to 9.

While not shown, these articles 20A, 20B may be alternatively constructed so that the front zone 42 and the intermediate zone 43 of the pad 22 are placed on the upper surface of the supporting sheet 35 and the rear zone 44 of the pad 22 is inserted toward the side of the front waist region 23 of the pants 21 through the slit 38 in order to attach the pad 22 to the pants 21 by means of the supporting sheet 35. In this case, the front zone 42 and the intermediate zone 43 extend over a generally rear half of the crotch region 24 of the pants 21 and the rear zone 44 extends over a generally front half of the pants 21 so that feces are guided through the opening 45 into the space 46 of the pad 22 and, at the same time, absorbed and retained by the core 41.

While not shown, these articles 20A, 20B may be alternatively constructed so that the distal rear zone 57 of the joined sheet 47 is eliminated and this joined sheet 47 comprises the proximal inner peripheral zone 55 and the distal front zone 56. The lower surface of the distal front zone 56 of the joined sheet 47 is fastened to the upper surface of the supporting sheet 35 by which the pad 22 is attached to the pants 21.

While the articles 20A, 20B are illustrated in which the hook members 58, 59 are attached to the lower surface of the joined sheet 47, these hook members 58, 59 may be replaced by pressure-sensitive adhesives coated on the lower surface of the joined sheet 47. In this case, the adhesives should be protectively covered with a release paper. While the articles 20A, 20B are illustrated in which the supporting sheet 35 is formed with the slit 38, the supporting sheet 35 may be formed with an elliptical opening (insertion opening) which is relatively long in the transverse direction, instead of the slit 38. It is possible to form the pants 21 by a woven fabric or knitted work instead of the nonwoven fabric. While the first opening 45 is illustrated to extend over the front zone 42 and the intermediate zone 43 of the pad 22, the opening 45 may extend at least over the intermediate zone 43 of these two zones 42, 43.

The article 20A may be alternatively constructed so that the water-pervious sheets 73 attached to the board 49 is made of an elastically stretchable/contractible fibrous nonwoven fabric. When the water-pervious sheets 73 is made of such stretchable/contractible fibrous nonwoven fabric, it is unnecessary to attach the elastic members 76 to the water-pervious sheets 73. The water-pervious sheets 73 is preferably modified to become hydrophilic. In the article 20A, it is not essential that the water-pervious sheets 73 is attached to the board 49.

Stock materials for the upper sheet 39 and the lower sheet 40 may be selected from, in addition to the composite sheet, composed of a hydrophobic fibrous nonwoven fabric, breathable liquid-impervious plastic film, and a composite nonwoven fabric comprising two or more hydrophobic fibrous nonwoven fabric layers laminated together. The supporting sheet 35 may be formed using, in addition to the stretchable/contractible fibrous nonwoven fabric, the other material selected from the group consisting of an inelastic hydrophobic fibrous nonwoven fabric, breathable liquid-impervious plastic film, a composite sheet comprising an inelastic hydrophobic fibrous nonwoven fabric and breathable liquid-impervious plastic film laminated together, and a composite nonwoven fabric comprising two or more inelastic hydrophobic fibrous nonwoven fabric layers laminated together. The joined sheet 47 may be formed using, in addition to the urethane foam, the other materials selected from the group consisting of a stretchable/contractible hydrophobic fibrous nonwoven fabric, inelastic hydrophobic fibrous nonwoven fabric, breathable liquid-impervious plastic film, a composite sheet comprising an inelastic hydrophobic fibrous nonwoven fabric and breathable liquid-impervious plastic film laminated together, and a composite nonwoven fabric comprising two or more inelastic hydrophobic fibrous nonwoven fabric layers. Stock materials for the upper and lower sheets 39, 40 as well as the supporting and joined sheets 35, 47 may be selected from the group consisting of various types of a composite nonwoven fabric (SM nonwoven fabric, SMS nonwoven fabric, SMMS nonwoven fabric) comprising a melt blown fibrous nonwoven fabric having a high water-resistance and a spun bond fibrous nonwoven fabric being high in strength as well as in flexibility laminated on at least one side of the melt blown fibrous nonwoven fabric.

Stock materials for the fibrous nonwoven fabric layer may be selected from the group consisting of spun lace-, needle punch-, melt blown-, thermal bond-, spun bond-, and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fiber selected from the group consisting of core-sheath conjugate fibers, side-by-side conjugate fibers, modified macaroni fiber, microporous fibers and fused type conjugate fibers.

The stretchable fibrous nonwoven fabric forming the supporting sheet 35 may be of a melt blown- or spun bond-nonwoven fibrous nonwoven fabric. As component fibers for such stretchable fibrous nonwoven fabric, stretchable fibers obtained by melt spinning thermoplastic elastomer resin may be used. It is possible without departing from the scope of the invention to form the supporting sheet 35 using a composite nonwoven fabric comprising a hydrophilic stretchable fibrous nonwoven fabric made of thermoplastic elastomer resin fibers and a hydrophilic fibrous nonwoven fabric made of crimped fibers obtained by melt spinning thermoplastic synthetic resin selected from the group consisting of polypropylene, polyethylene and polyester laminated on at least one surface of the hydrophilic stretchable fibrous nonwoven fabric.

As stock materials for the board 49, a virgin paper or waste paper may be used. The stock materials is not limited to the virgin paper and waste paper, the board 49 may be formed using the other materials such as an art paper, color board, coated paper, kraft paper, glassine, Kent paper, base paper as building material, cotton paper, high quality paper, medium quality paper, white lined board, drafting paper, moisture-proof paper, bond paper, marble paper, chip board, decorative laminate base paper and recycled paper.

Bonding of the upper and lower sheets 39, 40 to each other, bonding of the board 49 to the upper sheet 30, bonding of the core 41 to the lower sheet 40, bonding of the water-pervious sheets 73 to the board 49 and bonding of the elastic members 76 to the water-pervious sheets 73 may be carried out using adhesives or welding technique such as heat-sealing or sonic sealing. Adhesives may be selected from the group consisting of a hot melt adhesive, acrylic adhesive, rubber-based adhesive and the like.

What is claimed is:

1. A wearing article comprising:

a pants having front and rear waist regions opposed to each other, a crotch region extending between these waist regions, a waist-hole and a pair of leg-holes;

a disposable body waste absorbent pad having front and rear zones and an intermediate zone extending therebetween, said pad being adapted to be releasably attached to an inner side of said pants and said front zone and said intermediate zone or at least said intermediate zone of said pad with a first opening extending through an upper surface of said pad so that body waste having passed through said first opening is contained within said pad;

said pants being provided on the inner side thereof with a supporting sheet extending between said front and rear waist regions, said supporting sheet having longitudinally opposite fixed end portions bonded to respective peripheries of said front and rear waist regions and an intermediate zone extending between said fixed end portions, and said intermediate zone of said supporting sheet being formed in a longitudinally middle zone thereof with an insertion slit extending in a transverse direction so that the rear zone of said pad is inserted through said insertion slit;

said pad being provided on the upper surface thereof with a joined sheet attached to said upper surface and formed with a second opening contiguous to said first opening, said joined sheet having a fixed inner peripheral zone bonded to an opening's peripheral zone defining said first opening and a distal front zone extending forward from the front zone of said pad and releasably attached to said supporting sheet by means of fastener means; and said pad being attached to said pants by means of said supporting sheet by placing the front zone and the intermediate zone of said pad on an upper surface of said supporting sheet, inserting the rear zone of said pad through said insertion slit so as to be interposed between said pants and said supporting sheet and fastening the distal front zone of said joined sheet to the upper surface of said supporting sheet by means of said fastener means;

wherein said pad comprises a liquid-impervious upper sheet, a liquid-impervious lower sheet and a liquid-absorbent core interposed between these sheets and the core is bonded to the lower sheet, and said joined sheet is attached to an upper surface of said upper sheet so that a space adapted to contain said body wastes is formed between said upper sheet and said lower sheet.

2. The wearing article as defined by claim 1, further comprising a water-pervious sheet bonded directly, at a periphery thereof, to inner walls of said pad;
    wherein a middle portion of said water-pervious sheet is free of direct attachment to any of said upper sheet, said lower sheet and said core, and is spaced upward from the core.

3. The wearing article as defined by claim 2, wherein the middle portion of said water-pervious sheet covers a front portion of said core located below said first opening, without extending into the rear zone of said pad or covering a rear portion of said core positioned in the rear zone of said pad.

4. The wearing article as defined by claim 3, further comprising a plurality of elastic elements contractibly attached to the water-pervious sheet,
    wherein a tensile force of said elastic elements pulls the inner walls of said pad around said first opening towards one another, causing a peripheral edge of said first opening to rise above said water-pervious sheet and the water-pervious sheet, in turn, to rise above said core.

5. The wearing article as defined by claim 1, wherein said space is defined between the upper sheet and the core in both the rear zone of said pad, which is inserted through said insertion slit and located below the supporting sheet, and the front zone of said pad, which is located above both the supporting sheet.

6. The wearing article as defined by claim 1, wherein the fixed inner peripheral zone of said joined sheet around the second opening is bonded to the upper sheet in the peripheral zone of said first opening.

7. The wearing article as defined by claim 6, wherein the joined sheet is hydrophobic or liquid-impervious.

8. The wearing article as defined by claim 7, wherein the supporting sheet is hydrophobic or liquid-impervious.

9. A disposable absorbent pad for use with pants which have front and rear waist regions opposed to each other, a crotch region extending between said waist regions, a waist-hole, a pair of leg-holes, and a supporting sheet extending between said front and rear waist regions, said supporting sheet having longitudinally opposite fixed end portions bonded to respective peripheries of said front and rear waist regions and an intermediate zone extending between said fixed end portions, and said intermediate zone of said supporting sheet being formed in a longitudinally middle zone thereof with an insertion slit which extends in a transverse direction and through which a rear zone of said pad is insertable, said pad comprises:
    a liquid-impervious upper sheet having therethrough a first opening in a front zone of said pad;
    a liquid-impervious lower sheet;
    a liquid-absorbent core interposed between said upper and lower sheets, and bonded to the lower sheet so that a space adapted to contain body wastes is formed between said upper sheet and said core;
    a joined sheet having a second opening corresponding to said first opening, said joined sheet being attached to an upper surface of said upper sheet around said first opening; and
    fastening elements on said joined sheet for releasably attaching said joined sheet, and hence said pad, to the supporting sheet of the pants after the rear zone of said pad has been inserted through the insertion slit.

10. The absorbent pad as defined by claim 9, further comprising a water-pervious sheet bonded directly, at a periphery thereof, to inner walls of said pad defined by a lower surface of said upper sheet;
    wherein a middle portion of said water-pervious sheet is free of direct attachment to any of said upper sheet, said lower sheet and said core, and is spaced upward from the core.

11. The absorbent pad as defined by claim 10, further comprising a plurality of elastic elements contractibly attached to the water-pervious sheet;
    wherein a tensile force of said elastic elements pulls the inner walls of said pad around said first opening towards one another, causing a peripheral edge of said first opening to rise above said water-pervious sheet and the water-pervious sheet, in turn, to rise above said core.

* * * * *